United States Patent [19]

Schelbeck

[11] Patent Number: Plant 5,321

[45] Date of Patent: Nov. 6, 1984

[54] BEGONIA PLANT NAMED NINON

[75] Inventor: Erland V. Schelbeck, Odense, Denmark

[73] Assignee: L. Daehnfeldt Ltd., Odense, Denmark

[21] Appl. No.: 420,522

[22] Filed: Sep. 20, 1982

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A slow growing vigorous hybrid begonia named Ninon having very large peach/pink colored flowers, often with several whorls of tepals in the center, and excellent keeping qualities in all seasons.

1 Drawing Figure

The present invention relates to a new and distinct cultivar of begonia plant, botanically known as *Begonia hiemalis* (Fotsch), and known by the cultivar name Ninon.

The new cultivar was discovered by me as a seedling from a controlled crossing of my tuberous seedling P-156 as the seed parent with begonia Socotrana as the pollen parent. Asexual reproduction by stem cuttings has reproduced the unique features of the new cultivar through successive propagations.

The following characteristics distinguish the new begonia from both its parents and other begonias commercially known and used in the floriculture industry:

1. The foliage of Ninon lacks the pubescence of the tuberous parent. The plant is more compact, vigorous, and strong upright growth than P-156.

2. Whereas the pollen parent has small pink single type flowers, light foliage, and a general weak appearance, Ninon has very large compound camellia type flowers upwards to 6–7 cm. in diameter and a peach-/pink flower color. Also, Ninon is a vigorous grower with dark green large foliage.

3. Flower color is a brighter, more vivid shade of peach, and has larger flowers than Harmony (U.S. Plant Pat. No. 4,742). The foliage of Ninon is darker and larger than that of Harmony.

4. Many flowers are compound having several whorls of interior petals. In the illustration, the larger flower in the right hand group has four such whorls.

5. The flower color is distinct for this type of begonia.

6. The flower size approaches that of large flowering tuberous types. However, the weight and size of the flower does not cause flower drop as in many tuberous types.

7. The flower keeping quality is similar to that of Barbara, disclosed and claimed in my copending application Ser. No. 420,498, filed Sept. 20, 1982. As in Barbara, the flower color retention is very good with little fading, and individual flowers will remain in flower for several weeks. 8. Ninon is difficult to propagate by leaf cuttings and is generally propagated by top or stem cuttings.

9. Growth would be considered slow but this disadvantage is more than offset by the superior flower color, flower size, and keeping qualities.

The accompanying colored photograph taken March 1982 illustrates in perspective view the overall appearance of Ninon grown in a 25 cm. hanging basket, and shows the colors as true as it is reasonably possible to obtain in a colored reproduction of this type.

The following is a detailed description of my new begonia cultivar based on plants produced under commercial practices in Odense, Denmark and Ashtabula, Ohio. Color references are made to The Royal Horticultural Society Colour Chart except where general color terms of ordinary dictionary significance are used.

PARENTAGE

A controlled cross of begonia tuberous hybrida P-156 and begonia Socotrana.

PROPAGATION

Type of cutting: Stem.

Time to root to planting: 24–30 Days at 21° C. summer; 35–40 days at 21° C. winter.

Rooting habit: Quite uniform, dendritic, and fibrous.

PLANT DESCRIPTION

Form: Extremely short, vigorous, compact growth. Stem cutting must be tip pinched to force out lateral growth for maximum display; herbaceous.

Habit of growth: Upright, somewhat slow, needs to be pinched to force branching, needs extra time to fill out for maximum display.

Foliage: Simple, opposite; firm to crisp; large, necessitating leaf pruning.

(1) *Size.*—Leaf size can be quite variable on this cultivar depending on growing practices and environment; from 5–6 cm. up to 15 cm.

(2) *Shape.*—Generally ovate, overlapping basal lobes.

(3) *Texture.*—Topside glabrous, underside rucose.

(4) *Margin.*—Crenate.

(5) *Color.*—Young foliage top side, yellow green 146A-B, red margin; underside greyed red 180B with green veins; mature foliage top side, nearly green 139A; underside 147C with slight red infusion.

(6) *Venation.*—Palmate.

FLOWERING DESCRIPTION

Flowering habits: Will flower with ease in autumn, winter and spring. Summer flowering occurs best with controlled daylength and use of growth regulators. Flowers presented in raceme.

Natural flowering season: Mid-October through May. Indeterminent for day length, but reduced light energy needed to develop uniform flowering in summer.

Flower bud description: Flat and oval to nearly round.

Flowers borne: On raceme with progressive flowering over a considerable period of time; flower peduncles and pedicels are short, thick, and sturdy.

Quantity: Not highly floriferous but large compound flowers up to 6–7 cm. in diameter offset this characteristic.

Tepals:

(1) *Shape.*—Oval to round with basal tepals having frilled edges.

(2) *Color.*—Top side in winter when just opening, red 39-B to darker than red 38A when expanded, with very little fading at anytime; underside near 38A-B.

(3) *Number of tepals.*—From 16 to 30 or more on compound flowers.

(4) *Size of tepals.*—Basal tepals up to 3 cm.; interiors 1.5–2 cm.

(5) *Flower size.*—Up to 6–7 cm. in diameter.

Reproductive organs: Sterile, triploid, hybrid.

I claim:

1. A new and distinct cultivar of begonia named Ninon, as described and illustrated, and particularly characterized by its vigorous growth habit; large dark green foliage; large flowers which frequently are compound with several whorls of interior petals; distinct peach-/pink flower color, and its excellent keeping qualities.

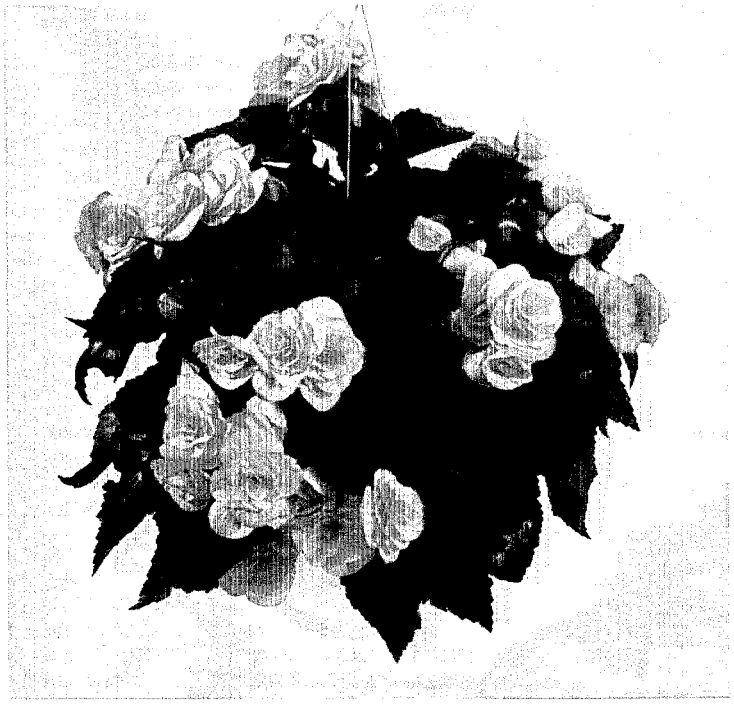

* * * * *